(12) United States Patent
Lee et al.

(10) Patent No.: US 6,680,386 B2
(45) Date of Patent: Jan. 20, 2004

(54) PROCESS FOR PREPARING 2-(4-CHLOROBENZOYLAMINO)-3-[2(1H)-QUINOLINON-4-YL] PROPIONIC ACID

(75) Inventors: Byoung-suk Lee, Seoul (KR); Myung-hee Chun, Seoul (KR)

(73) Assignee: Kyung Dong Pharm., Co., Ltd., Kyunggi-do (KR)

( * ) Notice: Subject to any disclaimer, the term of this patent is extended or adjusted under 35 U.S.C. 154(b) by 0 days.

(21) Appl. No.: 10/240,728

(22) PCT Filed: Feb. 20, 2002

(86) PCT No.: PCT/KR02/00262
§ 371 (c)(1),
(2), (4) Date: Oct. 8, 2002

(87) PCT Pub. No.: WO02/066436
PCT Pub. Date: Aug. 29, 2002

(65) Prior Publication Data
US 2003/0087930 A1 May 8, 2003

(30) Foreign Application Priority Data
Feb. 20, 2001 (KR) .......................................... 2001-8407

(51) Int. Cl.$^7$ ...................... C07D 215/16; C07D 215/20
(52) U.S. Cl. ........................................ 546/157; 546/158
(58) Field of Search ................................. 546/157, 158; 560/39, 38

(56) References Cited

U.S. PATENT DOCUMENTS

| 4,578,381 A | | 3/1986 | Uchida et al. | |
| 5,093,364 A | * | 3/1992 | Richards et al. | ............ 514/533 |

FOREIGN PATENT DOCUMENTS

| JP | 60019767 | 1/1985 |
| JP | 1308258 | 12/1989 |
| JP | 2049774 | 2/1990 |
| JP | 8295673 | 3/1996 |
| JP | 8295673 | 11/1996 |

* cited by examiner

Primary Examiner—D. Margaret Seaman
(74) Attorney, Agent, or Firm—Shlesinger, Arkwright & Garvey LLP

(57) ABSTRACT

The invention relates to a novel method for preparing 2-(4-chlorobenzoylamino)-3-[2(1H)-quinolinon-4-yl] propionic acid, also known as Rebamipide represented by the formula I and useful for treatment of peptic ulcer from alkyl 2-(4-chlorobenzoylamino)-2-alkoxycarbonyl-3-[2(1H)-quinolinon-4-yl]propionate represented by the formula II in the presence of a base solution for hydrolysis and decarboxylation to remove a carboxyl group.

9 Claims, No Drawings

PROCESS FOR PREPARING 2-(4-CHLOROBENZOYLAMINO)-3-[2(1H)-QUINOLINON-4-YL] PROPIONIC ACID

TECHNICAL FIELD

The present invention relates to a novel method for preparing 2-(4-chlorobenzoylamino)-3-[2(1H)-quinolinon-4-yl]propionic acid, also known as Rebamipide represented by the formula I and useful for treatment of peptic ulcer from alkyl 2-(4-chlorobenzoylamino)-2-alkoxycarbonyl-3-[2(1H)-quinolinon-4-yl]propionate represented by the formula II in the presence of a base solution for hydrolysis and decarboxylation to remove a carboxyl group:

[Formula I]

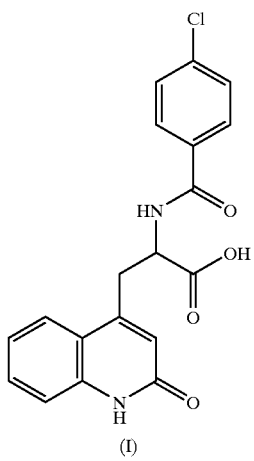

(I)

[Formula II]

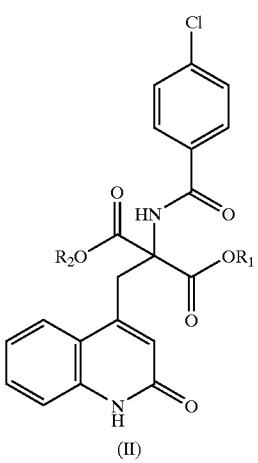

(II)

where $R_1$ and $R_2$ are lower alkyl or aryl.

BACKGROUND ART

In general, the conventional method for preparing the compound of the formula I involves the reaction of 4-bromomethylcarbostyril represented by the formula VII with diethyl acetamidomalonate represented by the formula. VIII in the presence of sodium ethylate as a base to prepare ethyl 2-acetamido-2-carboethoxy-3-[2(1H)-quinolinon-4-yl]propionate represented by the formula IX, the hydrolysis of the ethyl 2-acetamido-2-carboethoxy-3-[2(1H)-quinolinon-4-yl]propionate in 20% hydrochloric acid to prepare 2-amino-3-[2(1H)-quinolinon-4-yl]propionic acid hydrochloride represented by the formula X, and the condensation reaction of 2-amino-3-[2(1H)-quinolinon-4-yl]propionic acid hydrochloride with 4-chlorobenzoylchloride represented by the formula XI in the presence of potassium carbonate as a base to prepare 2-(4-chlorobenzoylamino)-3-[2(1H)-quinolinon-4-yl]propionic acid, also known as Rebamipide represented by the formula I. This preparation process can be expressed by the scheme 1:

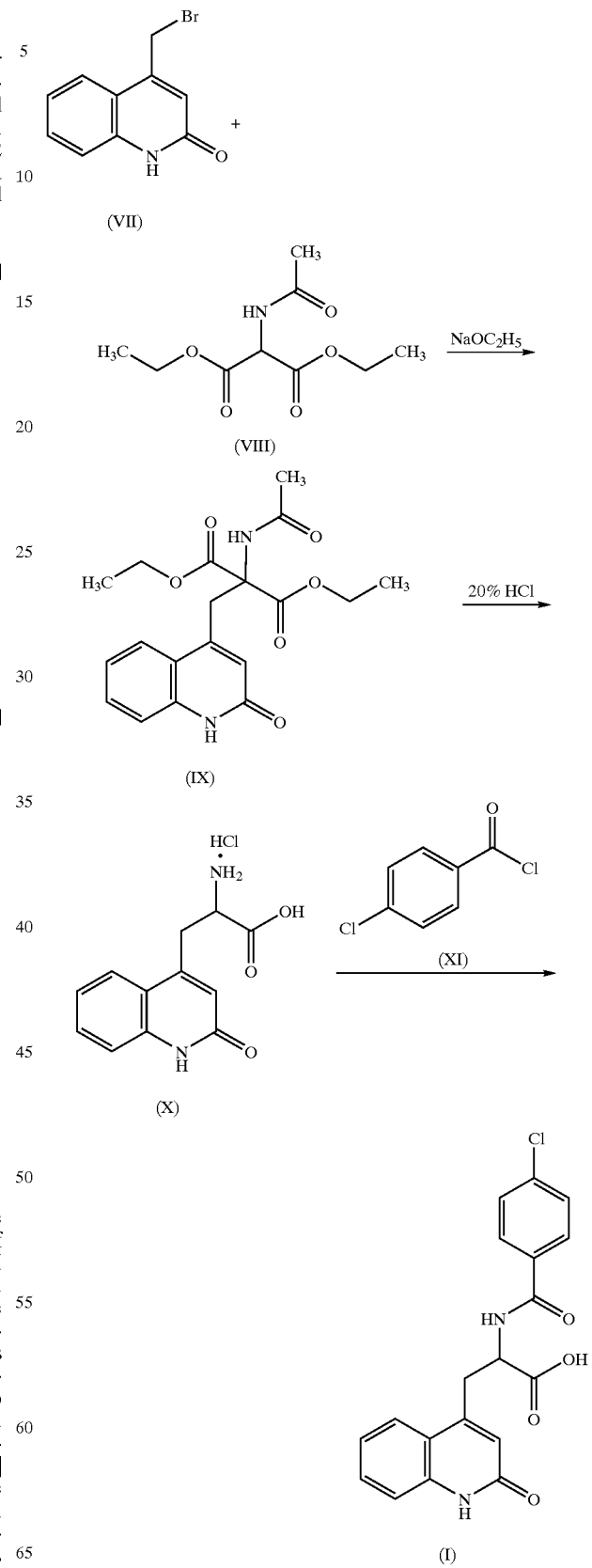

Scheme 1

The conventional preparation method is disadvantageous in the two following aspects. First, the hydrolysis of the compound of the formula IX to prepare the compound of the formula X involves more than 9 hours of reflux stirring using a halogenated hydracid such as 20% hydrochloric acid or hydrobromic acid. The use of such a dangerous strong acid as hydrochloric acid or hydrobromic acid causes a problem in regard to work stability and the flux stirring at a high temperature for a long time consumes much energy. So the preparation process is uneconomical and not friendly to the environment.

Second, the compound of the formula X prepared by the hydrolysis of the compound of the formula IX is no more than an intermediate and has to be reacted with the compound of the formula XI for condensation reaction in order to yield the title compound of the formula I. This makes the process long and thus reduces the yield.

DISCLOSURE OF INVENTION

In an attempt to solve the problems with the prior art, the inventors of the present invention have explored a novel preparation method that provides a high yield with a more economical, safer and simpler process.

Accordingly, it is an object of the present invention to provide a novel method for preparing 2-(4-chlorobenzoylamino)-3-[2(1H)-quinolinon-4-yl]propionic acid, so-called Rebamipide that is a material for treatment of peptic ulcer.

In an aspect of the present invention, there is provided a method for providing, with a high yield, 2-(4-chlorobenzoylamino)-3-[2(1H)-quinolinon-4-yl]propionic acid, also known as Rebamipide represented by the formula I and useful for treatment of peptic ulcer:

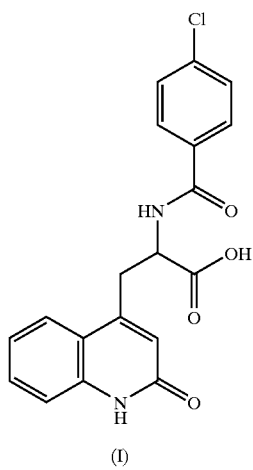

[Formula (I)]

More specifically, as shown in the following scheme 2, the present invention is to provide a method for preparing Rebamipide of the formula I with high yield (92%) and purity that includes subjecting the compound of the formula II to both hydrolysis and decarboxylation in the presence of a base at a temperature of −10 to 80° C., preferably 50 to 60° C. in an alcoholic solvent or a mixed solvent of at least one alcohol and water for 2 hours:

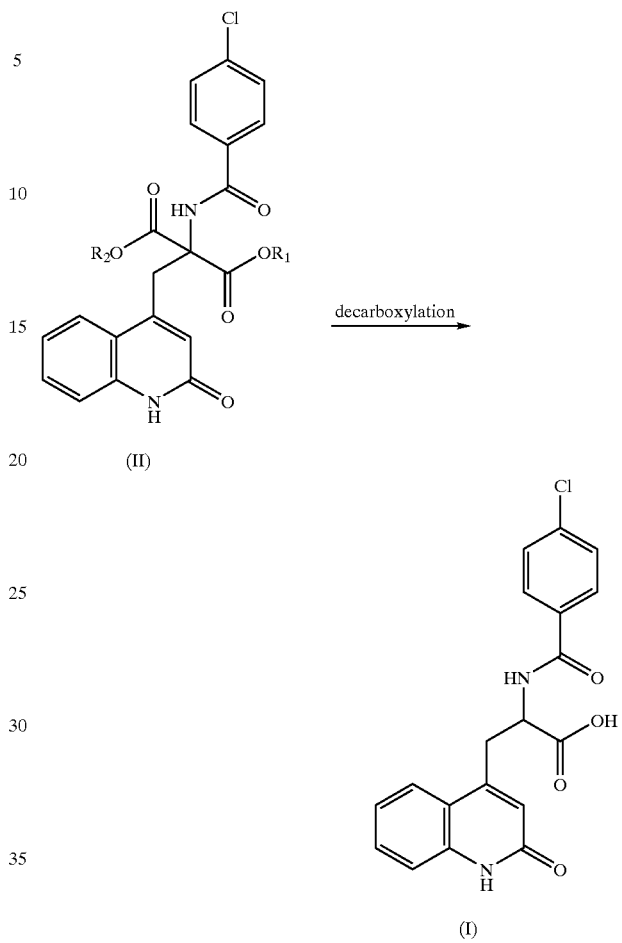

where $R_1$ and $R_2$ are lower alkyl or aryl.

In the preparation method of the present invention, the base solution used for the hydrolysis of the compound of the formula II may include, if not specifically limited to, sodium hydroxide or potassium hydroxide solution. The compound of the formula II is reacted in a mild condition, for example, at a preferable temperature of about 50 to 60° C. for about 2 hours for selective hydrolysis of the ester group and decarboxylation to yield the title compound of the formula I.

As an intermediate in the present invention, the compound of the formula II is prepared simply by reacting the compound of the formula IV with 4-halomethylquinolinon of the formula III in the presence of sodium ethylate with reflux stirring for 2 hours for condensation reaction, which process can be expressed by:

Scheme 3

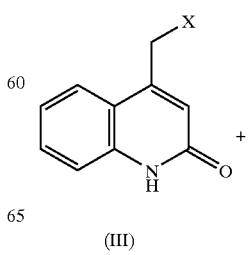

(III)

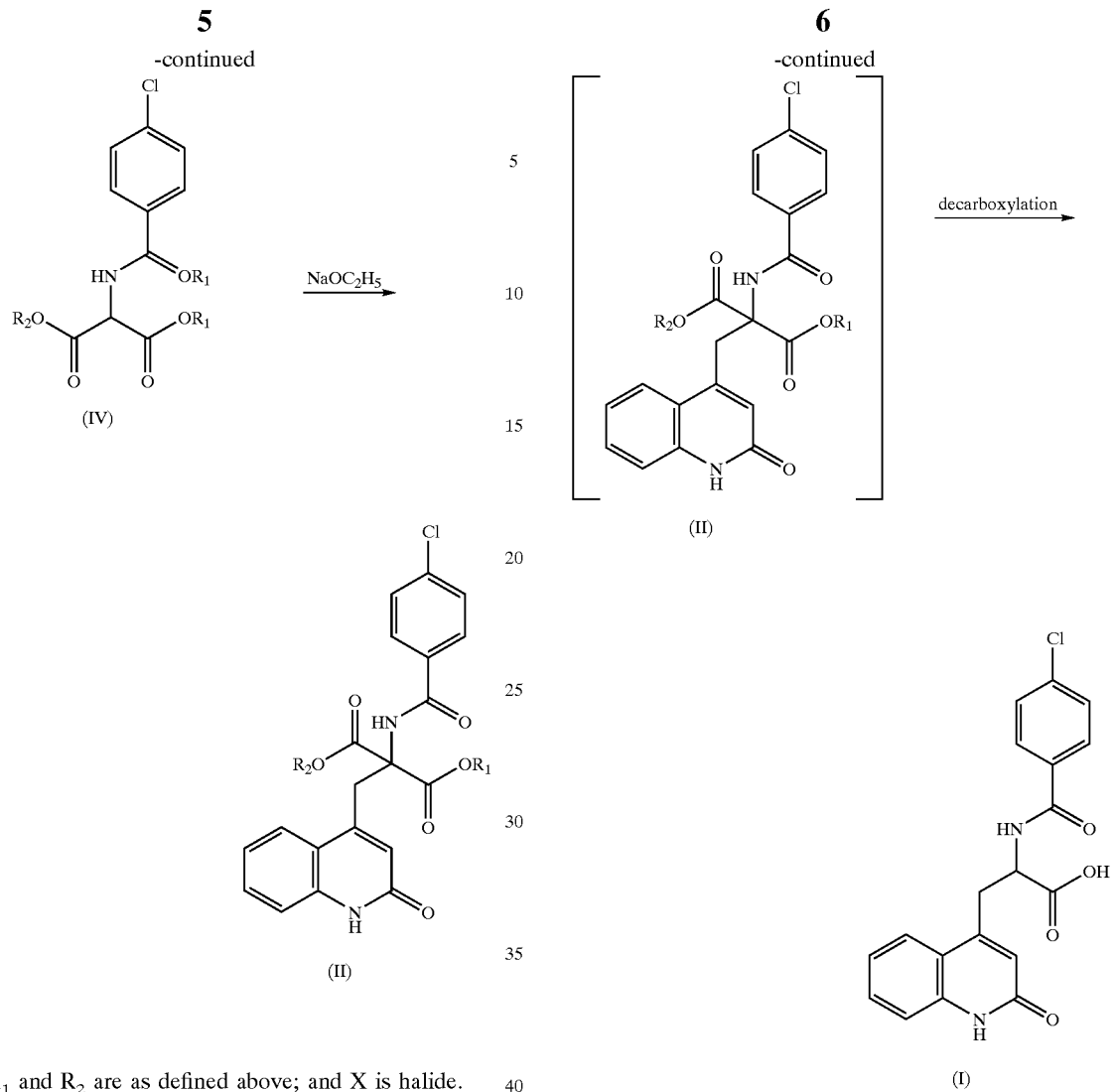

where R₁ and R₂ are as defined above; and X is halide.

Preferably, the compound of the formula II prepared by the scheme 3 is not isolated or purified but the reactant solution is subjected to thin layer chromatography to check the termination of the reaction, immediately after which the compound of the formula I is yielded according to the scheme 2. The overall preparation process can be expressed by:

Scheme 4

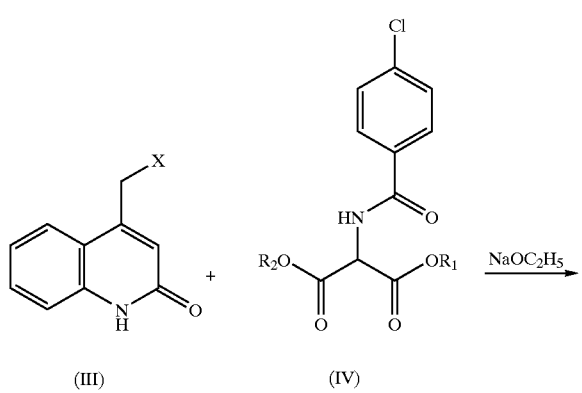

where $R_1$, $R_2$ and X are as defined above.

The method for preparing Rebamipide of the formula I without a step of isolating and purifying the compound of the formula II can be summarized as follows. First, the compound of the formula II is prepared by reacting the compound of the formula IV with the compound of the formula III in the presence of sodium ethylate at the room temperature with stirring for 16 hours for condensation reaction. Without isolation or purification of the compound of the formula II, the reactant solution containing the compound of the formula II is subjected to both hydrolysis and decarboxylation in the presence of a base at a temperature of −10 to 80° C., preferably 50 to 60° C. in an alcoholic solvent or a mixed solvent of at least one alcohol and water for about 2 hours to produce Rebamipide of the formula I with high yield and purity.

In the case of preparing Rebamipide of the formula I without isolation or purification of the compound of the formula II according to the present invention, the compound of the formula II is subjected to a reaction in a mild condition at the room temperature instead of reflux stirring in the synthesis process, thereby increasing the yield, and the step of isolation or purification is eliminated to reduce the complexity of the process.

On the other hand, the compound of the formula IV is simply prepared from the compound of the formula V and the compound of the formula VI, normally 4-chlorobenzoylchloride according to the following scheme 5:

Scheme 5

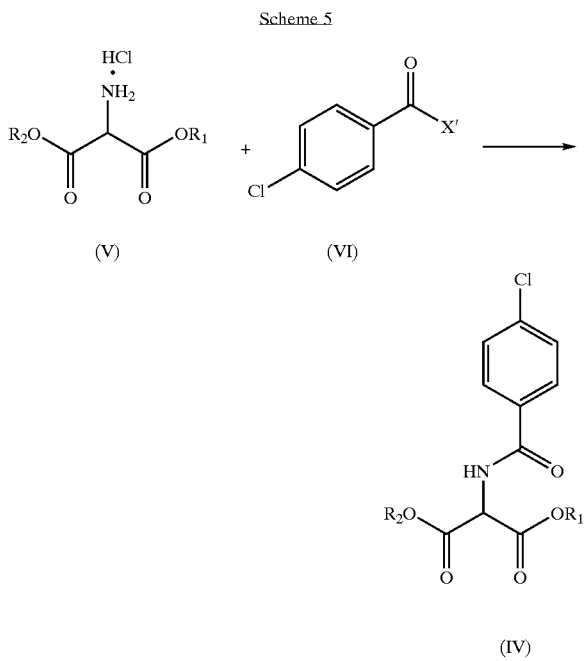

where $R_1$ and $R_2$ are as defined above; and X' is halogen or hydroxy.

The preparation method of the present invention includes no more than one or two reaction steps to prepare the title compound of the formula I from the compound of the formula III without the complicated reaction step of the prior art that requires strict conditions, thereby reducing the number of reaction steps for the preparation process, and needs a mild condition (for example, low reaction temperature) without using such a strong acid as hydrochloric acid or hydrobromic acid. So the present invention provides an environment-friendly and economical method for preparing Rebamipide of the formula I with a high yield (about 92%).

If necessary, the title compound of the formula I in the present invention is convertible to its physiologically or pharmaceutically acceptable hydrate and/or acid addition salt.

BRIEF DESCRIPTION OF THE DRAWINGS

BEST MODE FOR CARRYING OUT THE INVENTION

Hereinafter, the present invention will be described in detail by way of the following examples, which are not intended to limit the scope of the present invention.

EXAMPLE 1

Synthesis of Diethyl 4-chlorobenzamidomalonate 5.00 g of diethyl aminomalonate hydrochloride and 4.78 g of triethylamine were added to 100 ml of chloroform, and the resulting solution was stirred at the room temperature for 30 minutes. After cooling down the solution to 10° C., 4.13 g of 4-chlorobenzoylchloride was slowly added to the solution and the resulting solution was stirred at the room temperature for 2 hours. Upon the completion of the reaction, the solution was washed with 20 ml of water and 20 ml of 5% sodium bicarbonate and the organic layer was subjected to dry filtration to yield 6.70 g (90.4%) of diethyl 4-chlorobenzamidomalonate.

Melting point: 89.5~90.3° C.; and

1H NMR (CDCl$_3$, 500 MHz)(ppm): 1.31–1.34 (m,6H), 4.28–4.35 (m,4H), 5.31–5.32 (d,1H), 7.09–7.10 (br,1H), 7.43–7.45 (m,2H), 7.78–7.81 (m,2H).

EXAMPLE 2

Synthesis of Diethyl 4-chlorobenzamidomalonate 1.00 g of 4-chlorobenzoic acid and 1.45 g of dicyclohexylcarbodiimide (DCC) were solved in 30 ml of tetrahydrofuran, and the resulting solution was stirred at the room temperature for 2 hours. Subsequently, 1.35 g of diethyl aminomalonate hydrochloride and 0.65 g of triethylamine were added to 20 ml of tetrahydrofuran, and after stirring for about 20 minutes, the previously prepared solution was added to the this resulting solution. The mixed solution was then stirred at the room temperature for 2 hours to complete the reaction. After filtration of the solution and concentration of the filtrate, the concentrated filtrate was diluted with 50 ml of chloroform, washed with 20 ml of water twice and subjected to dry filtration to yield 1.72 g (86%) of diethyl 4-chlorobenzamidomalonate.

The data of melting point and 1H NMR were the same as those in Example 1.

EXAMPLE 3

Synthesis of Ethyl 2-(4-chlorobenzoylamino)-2-ethoxycarbonyl-3-[2(1H)-quinolinon-4-yl]propionate Sodium ethylate was prepared from 0.48 g of sodium and 100 ml of anhydrous ethyl alcohol. After adding 6.59 g of diethyl 4-chlorobenzamidomalonate, the mixture was stirred at the room temperature for one hour. 5.00 g of 4-bromomethylcarbostyril was added and the mixture was subjected to reflux stirring for 2 hours. After the completion of the reaction, the ethyl alcohol was removed through vacuum distillation and water was added to the residue for crystallization. The crystal thus obtained was filtered and dried to yield 8.02 g (81.1%) of ethyl 2-(4-chlorobenzoylamino)-2-ethoxycarbonyl-3-[2(1H)-quinolinon-4-yl]propionate.

Melting point: 213.3~214.5° C.; and

1H NMR (CDCl$_3$, 500 MHz) (ppm): 1.29–1.32 (m,6H), 4.05 (s,2H), 4.24–4.36 (m,4H), 6.45 (s,1H), 6.98–7.00 (m,1H), 7.33–7.41 (m,4H), 7.54–7.56 (m,1H), 7.70–7.71 (d,2H), 12.19 (br,1H).

EXAMPLE 4

Synthesis of 2-(4-chlorobenzoylamino)-3-[2(1H)-quinolinon-4-yl]propionic Acid 2.31 g of sodium hydroxide was completely dissolved in 50 ml of water and 150 ml of ethyl alcohol with stirring. Subsequently, 10 g of ethyl 2-(4-chlorobenzoylamino)-2-ethoxycarbonyl-3-[2(1H)-qunolinon-4-yl]propionate was added to the above solution and the resulting solution was stirred at 50° C. for 2 hours. After the completion of the reaction, the ethyl alcohol was removed through vacuum concentration and 1N HCl was added to the residue for crystallization. The crystal thus obtained was filtered and then subjected to recrystallization with DMF and water to yield 7.30 g (92%) of 2-(4-chlorobenzoylamino)-3-[2(1H)-quinolinon-4-yl]propionic acid.

Melting point: 288.2~288.9° C. (dec.); and

1H NMR (DMSO-d6, 500 MHz) (ppm): 3.20–3.51 (m,2H), 4.704.75 (m,1H), 6.44 (s,1H), 7.22–7.25 (m,1H), 7.30–7.32 (d,1H), 7.48–7.56 (m,3H), 7.80–7.84 (m,3H), 8.89–8.91 (d,1H), 11.65 (s,1H).

EXAMPLE 5

Synthesis of 2-(4-chlorobenzoylamino)-3-[2(1H)-quinolinon-4-yl]propionic Acid 3.50 g of potassium hydroxide was completely dissolved in 50 ml of water and 150 ml of ethyl alcohol with stirring. Subsequently, 10 g of ethyl 2-(4-chlorobenzoylamino)-2-ethoxycarbonyl-3-[2(1H)-qunolinon-4-yl]propionate was added to the above solution and the resulting solution was stirred at 50° C. for 2 hours. After the completion of the reaction, the ethyl alcohol was removed through vacuum concentration and 1N HCl was added to the residue for crystallization. The crystal thus obtained was filtered and then subjected to recrystallization with DMF and water to yield 7.20 g (91.5%) of 2-(4-chlorobenzoylamino)-3-[2(1H)-quinolinon-4-yl]propionic acid.

The data of melting point and 1H NMR were the same as those in Example 4.

EXAMPLE 6

Synthesis of 2-(4-chlorobenzoylamino)-3-[2(1H)-quinolinon-4-yl]propionic Acid 2.31 g of sodium hydroxide was completely dissolved in 200 ml of ethyl alcohol with stirring. Subsequently, 10 g of ethyl 2-(4-chlorobenzoylamino)-2-ethoxycarbonyl-3-[2(1H)-qunolinon-4-yl]propionate was added to the above solution and the resulting solution was stirred at 50° C. for 2 hours. After the completion of the reaction, the ethyl alcohol was removed through vacuum concentration and 1N HCl was added to the residue for crystallization. The crystal thus obtained was filtered and then subjected to recrystallization with DMF and water to yield 7.12 g (90.2%) of 2-(4-chlorobenzoylamino)-3-[2(1H)-quinolinon-4-yl]propionic acid.

The data of melting point and 1H NMR were the same as those in Example 4.

EXAMPLE 7

Synthesis of 2-(4-chlorobenzoylamino)-3-[2(1H)-quinolinon-4-yl]propionic Acid 3.50 g of potassium hydroxide was completely dissolved in 200 ml of ethyl alcohol with stirring. Subsequently, 10 g of ethyl 2-(4-chlorobenzoylamino)-2-ethoxycarbonyl-3-[2(1H)-qunolinon-4-yl]propionate was added to the above solution and the resulting solution was stirred at 50° C. for 2 hours. After the completion of the reaction, the ethyl alcohol was removed through vacuum concentration and 1N HCl was added to the residue for crystallization. The crystal thus obtained was filtered and then subjected to recrystallization with DMF and water to yield 7.18 g (91.2%) of 2-(4-chlorobenzoylamino)-3-[2(1H)-quinolinon-4-yl]propionic acid.

The data of melting point and 1H NMR were the same as those in Example 4.

EXAMPLE 8

Synthesis of 2-(4-chlorobenzoylamino)-3-[2(1H)-guinolinon-4-yl]propionic Acid 2.31 g of sodium hydroxide was completely dissolved in 50 ml of water and 150 ml of methyl alcohol with stirring. Subsequently, 10 g of ethyl 2-(4-chlorobenzoylamino)-2-ethoxycarbonyl-3-[2(1H)-qunolinon-4-yl]propionate was added to the above solution and the resulting solution was stirred at 50° C. for 2 hours. After the completion of the reaction, the methyl alcohol was removed through vacuum concentration and 1N HCl was added to the residue for crystallization. The crystal thus obtained was filtered and then subjected to recrystallization with DMF and water to yield 7.02 g (89.2%) of 2-(4-chlorobenzoylamino)-3-[2(1H)-quinolinon-4-yl]propionic acid.

The data of melting point and 1H NMR were the same as those in Example 4.

EXAMPLE 9

Synthesis of 2-(4-chlorobenzoylamino)-3-[2(1H)-quinolinon-4-yl]propionic Acid 100 ml of anhydrous ethyl alcohol and 2.23 g of sodium ethoxide (96%) were added to a 500 ml flask, and the mixture was cooled down to below 5° C. After adding 7.91 g of diethyl 4-chlorobenzamidomalonate, the resulting solution was stirred at below 5° C. for one hour. 5.00 g of 4-bromomethylquinolinon was added to the mixture and the resulting solution was stirred at the room temperature for 16 hours to produce an intermediate, ethyl 2-(4-chlorobenzoylamino)-2-ethoxycarbonyl-3-[2(1H)-quinolinon-4-yl]propionate. After the completion of the reaction, 2.71 g of sodium hydroxide (93%) was dissolved in 30 ml of purified water and this aqueous solution was added to the above solution, which was then stirred at the room temperature for about 2 hours. Subsequently, the resulting solution was warmed to about 60° C. and stirred for 2 hours to complete the reaction. The ethyl alcohol was removed through vacuum concentration, and purified water and 1N HCl were added to the residue for crystallization. The crystal thus obtained was filtered and then subjected to recrystallization with DMF and water to yield 7.18 g (92.17%) of 2-(4-chlorobenzoylamino)-3-[2(1H)-quinolinon-4-yl]propionic acid.

The data of melting point and 1H NMR were the same as those in Example 4.

EXAMPLE 10

Synthesis of 2-(4-chlorobenzoylamino)-3-[2(1H)-quinolinon-4-yl]propionic Acid 100 ml of anhydrous ethyl alcohol and 2.23 g of sodium ethoxide (96%) were added to a 500 ml flask, and the mixture was cooled down to below 5° C. After adding 7.91 g of diethyl 4-chlorobenzamidomalonate, the resulting solution was stirred at below 5° C. for one hour. 5.00 g of 4-bromomethylquinolinon was added to the mixture and the resulting solution was stirred at the room temperature for 16 hours to produce an intermediate, ethyl 2-(4-chlorobenzoylamino)-2-ethoxycarbonyl-3-[2(1H)-quinolinon-4-yl]propionate. After the completion of the reaction, 2.71 g of sodium hydroxide (93%) was dissolved in 30 ml of purified water and this aqueous solution was added to the above solution, which was then stirred at the room temperature for about 2 hours. Subsequently, the resulting solution was warmed to about 60° C. and stirred for 2 hours to complete the reaction. The ethyl alcohol was removed through vacuum concentration, and purified water and 1N HCl were added to the residue for crystallization. The crystal thus obtained was filtered and then subjected to recrystallization with methanol and potassium hydroxide to yield 6.7 g (86.0%) of 2-(4-chlorobenzoylamino)-3-[2(1H)-quinolinon-4-yl]propionic acid.

The data of melting point and 1H NMR were the same as those in Example 4.

EXAMPLE 11

Synthesis of 2-(4-chlorobenzoylamino)-3-[2(1H)-quinolinon-4-yl]propionic Acid 100 ml of anhydrous ethyl alcohol and 2.23 g of sodium ethoxide (96%) were added to a 500 ml flask, and the mixture was cooled down to below 5° C. After adding 7.91 g of diethyl 4-chlorobenzamidomalonate, the resulting solution was stirred at below 5° C. for one hour. 5.00 g of 4-bromomethylquinolinon was added to the mixture and the resulting solution was stirred at the room temperature for 16 hours to produce an intermediate, ethyl 2-(4-chlorobenzoylamino)-2-ethoxycarbonyl-3-[2(1H)-quinolinon-4-yl]propionate. After the completion of the reaction, 3.93 g of potassium hydroxide (90%) was dissolved in 30 ml of purified water and this aqueous solution was added to the above solution, which was then stirred at the room temperature for about 2 hours. Subsequently, the resulting solution was warmed to about 60° C. and stirred for 2 hours to complete the reaction. The ethyl alcohol was removed through vacuum concentration, and purified water and 1N HCl were added to the residue for crystallization. The crystal thus obtained was filtered and then subjected to recrystallization with DMF and water to yield 7.08 g (90.88%) of 2-(4-chlorobenzoylamino)-3-[2(1H)-quinolinon-4-yl]propionic acid.

The data of melting point and 1H NMR were the same as those in Example 4.

EXAMPLE 12

Synthesis of 2-(4-chlorobenzoylamino)-3-[2(1H)-quinolinon-4-yl]propionic Acid 100 ml of anhydrous ethyl alcohol and 2.23 g of sodium ethoxide (96%) were added to a 500 ml flask, and the mixture was cooled down to below 5° C. After adding 7.91 g of diethyl 4-chlorobenzamidomalonate, the resulting solution was stirred at below 5° C. for one hour. 5.00 g of 4-bromomethylquinolinon was added to the mixture and the resulting solution was stirred at the room temperature for 16 hours to produce an intermediate, ethyl 2-(4-chlorobenzoylamino)-2-ethoxycarbonyl-3-[2(1H)-quinolinon-4-yl]propionate. After the completion of the reaction, 2.71 g of sodium hydroxide (93%) was added to the above solution, which was then stirred at the room temperature for about 2 hours. Subsequently, the resulting solution was warmed to about 60° C. and stirred for 4 hours to complete the reaction. The concentrated hydrochloric acid were added to the residue for crystallization. The crystal thus obtained was filtered and then subjected to recrystallization with DMF and water to yield 7.15 g (91.78%) of 2-(4-chlorobenzoylamino)-3-[2(1H)-quinolinon-4-yl]propionic acid.

The data of melting point and 1H NMR were the same as those in Example 4.

EXAMPLE 13

Synthesis of 2-(4-chlorobenzoylamino)-3-[2(1H)-quinolinon-4-yl]propionic Acid 100 ml of anhydrous ethyl alcohol and 2.23 g of sodium ethoxide (96%) were added to a 500 ml flask, and the mixture was cooled down to below 5° C. After adding 7.91 g of diethyl 4-chlorobenzamidomalonate, the resulting solution was stirred at below 5° C. for one hour. 5.00 g of 4-bromomethylquinolinon was added to the mixture and the resulting solution was stirred at the room temperature for 16 hours to produce an intermediate, ethyl 2-(4-chlorobenzoylamino)-2-ethoxycarbonyl-3-[2(1H)-quinolinon-4-yl]propionate. After the completion of the reaction, 3.93 g of potassium hydroxide (90%) was added to the above solution, which was then stirred at the room temperature for about 2 hours. Subsequently, the resulting solution was warmed to about 60° C. and stirred for 4 hours to complete the reaction. The concentrated hydrochloric acid were added to the residue for crystallization. The crystal thus obtained was filtered and then subjected to recrystallization with DMF and water to yield 7.17 g (92.04%) of 2-(4-chlorobenzoylamino)-3-[2(1H)-quinolinon-4-yl]propionic acid.

The data of melting point and 1H NMR were the same as those in Example 4.

INDUSTRIAL APPLICABILITY

As described above, the preparation method of the present invention prepares the title compound, Rebamipide by no more than one or two reaction steps without the complicated reaction step of the prior art that requires strict conditions, thereby reducing the number of reaction steps for the preparation process, and needs a mild condition without using a strong acid. So the present invention provides an environment-friendly high-yield preparation method.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:

1. A method of preparing 2-(4-chlorobenzoylamino)-3-[2(1H)-quinolinon-4-yl]propionic acid represented by the formula I, the method comprising hydrolysis and decarboxylation reaction of a compound represented by the formula II to remove a carboxyl group:

[Formula I]

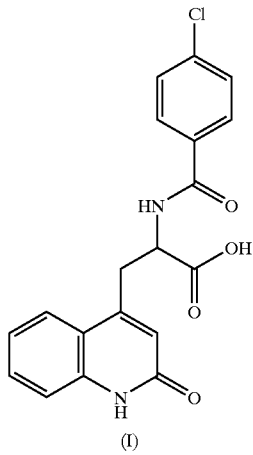

(I)

-continued

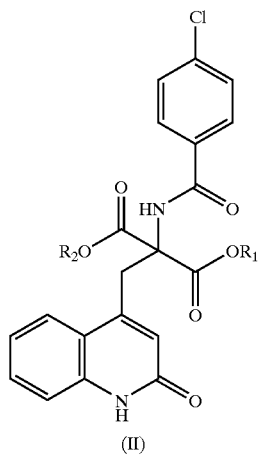

(II)

wherein R₁ and R₂ are lower alkyl or aryl.

2. The method as claimed in claim 1 wherein the reaction is performed at a temperature of −10 to 80° C. in an alcoholic solvent or a mixed solvent of alcohol and water.

3. The method as claimed in claim 2, wherein the alcohol includes methyl alcohol, ethyl alcohol or a mixture of them, the reaction being performed at a temperature of 50 to 60° C.

4. The method as claimed in claim 1, wherein the reaction is performed in the presence of a base.

5. The method as claimed in claim 4, wherein the base includes sodium hydroxide or potassium hydroxide.

6. The method as claimed in claim 1, wherein the compound of the formula II is prepared by reacting a compound represented by the formula III with a compound represented by the formula IV for condensation reaction:

[Formula II]

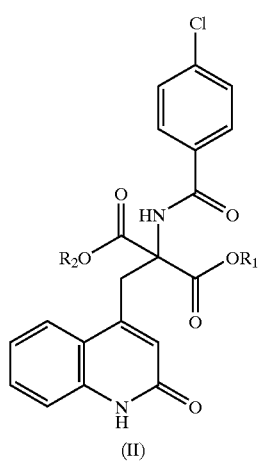

(II)

wherein R₁ and R₂ are lower alkyl or aryl;

[Formula III]

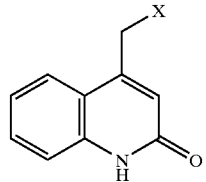

wherein X is a halogen atom; and

[Formula IV]

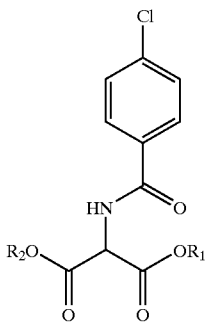

wherein R₁ and R₂ are lower alkyl or aryl.

7. The method as claimed in claim 6, wherein the compound of the formula IV is prepared from a compound represented by the formula V and a compound represented by the formula VI:

[Formula IV]

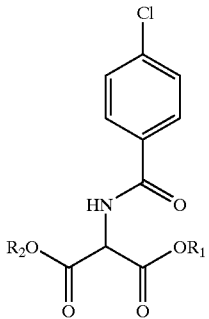

wherein R₁ and R₂ are lower alkyl or aryl;

[Formula V]

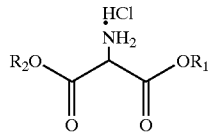

wherein $R_1$ and $R_2$ are lower alkyl or aryl; and

[Formula VI]

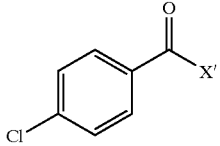

wherein X' is a halogen atom or hydroxy.

8. The method as claimed in claim 1, wherein the compound of the formula II is prepared from the compound of the formula III and the compound of the formula IV and then, without a step of isolation and purification after the completion of the reaction, removed of a carboxyl group through hydrolysis and decarboxylation to yield the 2-(4-chlorobenzoylamino)-3-[2(1H)-quinolinon-4-yl] propionic acid of the formula I according to the following scheme:

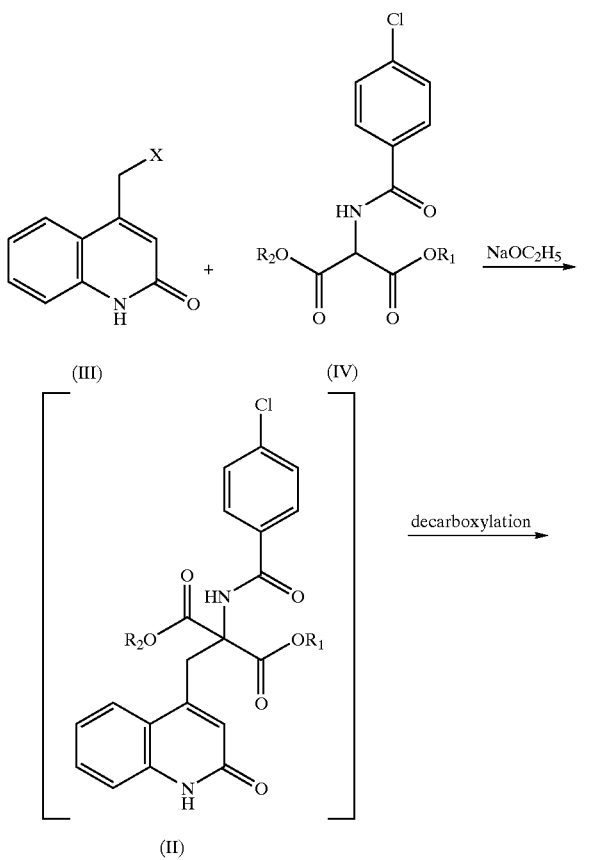

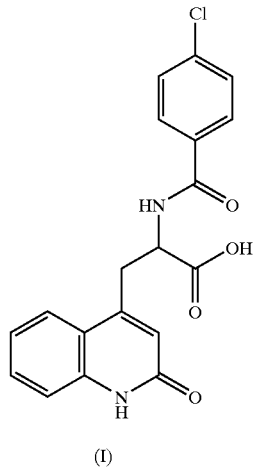

(I)

wherein $R_1$ and $R_2$ are lower alkyl or aryl; and X is a halogen atom.

9. A compound represented by the formula II:

[Formula II]

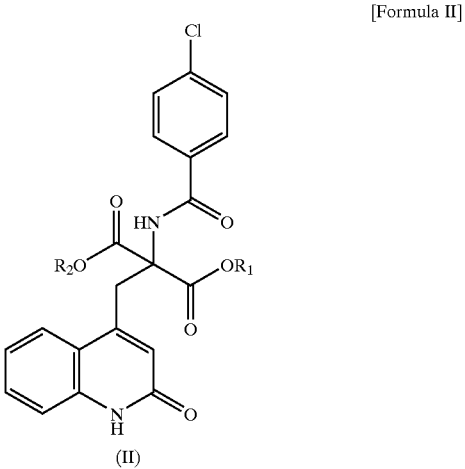

(II)

wherein $R_1$ and $R_2$ are lower alkyl or aryl.

* * * * *